United States Patent [19]
McNelis et al.

[11] Patent Number: 5,891,081
[45] Date of Patent: Apr. 6, 1999

[54] SUPPORTING RIM STRUCTURE OF AN OPEN INSERTION END TAMPON APPLICATOR USED TO POST FORM AN INSERTION END OF A TAMPON PLEDGET

[75] Inventors: Thomas C. McNelis; Michael L. Miller; Jamshid Rejai, all of Dover, Del.

[73] Assignee: Playtex Products, Inc., Westport, Conn.

[21] Appl. No.: 892,088

[22] Filed: Jul. 14, 1997

Related U.S. Application Data

[63] Continuation of Ser. No. 502,715, Jul. 14, 1995, abandoned.

[51] Int. Cl.⁶ .................................................. A61F 13/20
[52] U.S. Cl. ............................... 604/14; 604/904; 604/15
[58] Field of Search ............................... 604/11–18, 904, 604/285–288

[56] References Cited

U.S. PATENT DOCUMENTS

| | | |
|---|---|---|
| 2,077,231 | 4/1937 | Fourness et al. . |
| 2,355,628 | 8/1944 | Calhoun . |
| 2,386,590 | 10/1945 | Calhoun . |
| 2,799,055 | 7/1957 | Carrier . |
| 3,667,465 | 6/1972 | Voss . |
| 3,683,915 | 8/1972 | Voss . |
| 3,717,149 | 2/1973 | Morane . |
| 3,999,549 | 12/1976 | Poncy et al. . |
| 4,077,408 | 3/1978 | Murray et al. . |
| 4,479,791 | 10/1984 | Sprague ............................ 604/14 |
| 4,685,178 | 8/1987 | Nakanishi . |
| 5,330,421 | 7/1994 | Tarr et al. . |

*Primary Examiner*—John G. Weiss
*Assistant Examiner*—Dennis Ruhl
*Attorney, Agent, or Firm*—Ohlandt, Greeley, Ruggiero & Perle,L.L.P.

[57] ABSTRACT

There is provided a supporting rim structure of an open-ended tampon applicator for firmly supporting a tampon pledget that has been assembled in the applicator. The applicator supports the pledget around an intermediate section between its insertion end and its rear portion so that the insertion end is exposed outside of the applicator and the rear portion is inside of the applicator. In particular, the rim structure firmly supports the pledget against an axial force subjected to the pledget by a forming tool that forms the insertion end of the pledget into a rounded, hemispherical shape and yet readily allows the pledget to eject from the applicator. The rim structure has a shape that tapers angularly inward from the body of the applicator to form a rigid brace that counters the axial force subjected by the forming tool. Thus, while preventing the insertion end of the pledget from receding back into the applicator, the rim structure allows the pledget to easily eject from the applicator.

9 Claims, 3 Drawing Sheets

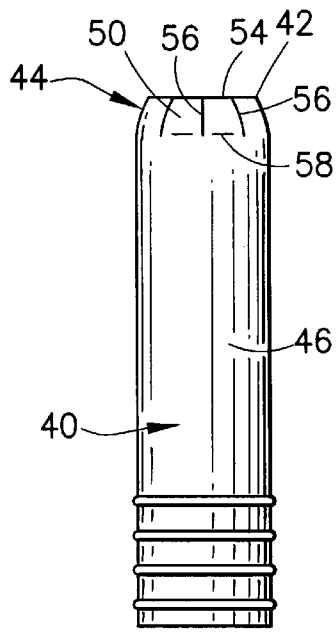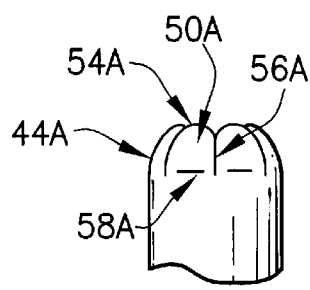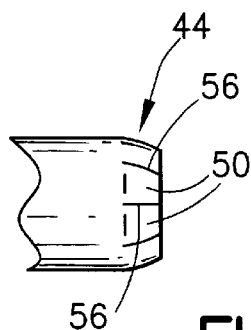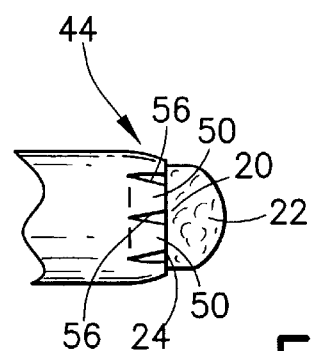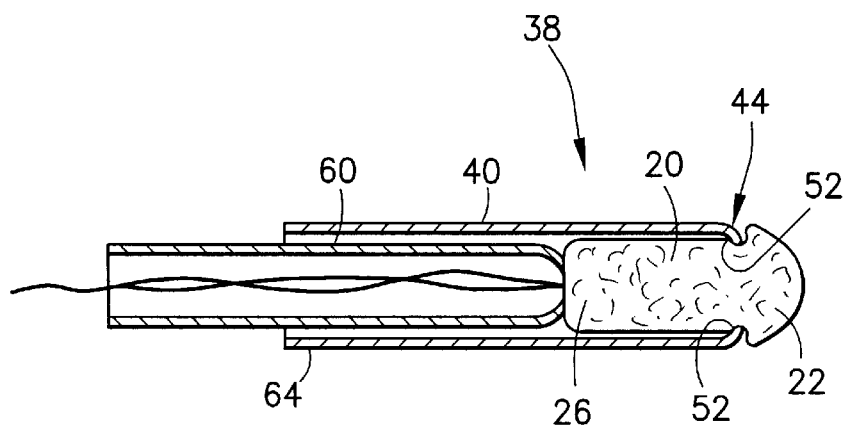

SUPPORTING RIM STRUCTURE OF AN OPEN INSERTION END TAMPON APPLICATOR USED TO POST FORM AN INSERTION END OF A TAMPON PLEDGET

This is a continuation of application Ser. No. 08/502,715, filed Jul. 14, 1995 now abandoned.

BACKGROUND OF THE INVENTION

I. Field of the Invention

The present invention relates generally to tampon assemblies. More particularly, the present invention relates to a supporting rim structure of an open insertion end tampon applicator that provides for an improved method for forming a rounded insertion end of a tampon pledget assembled therein.

A tampon assembly, including a tampon pledget and a tampon applicator, may have a rounded insertion end to facilitate the insertion of the tampon pledget into a vagina. The rounded insertion end may be formed on the applicator, such as a petal tip applicator, or a pledget that is positioned in the applicator, such as an open insertion end applicator.

For a petal tip applicator, curved flexible petals at the insertion end of the applicator enclose and cover a pledget within the applicator. Alternatively, for an open insertion end applicator, a pledget having a rounded insertion end extends from a blunt open end of the applicator. Since the exposed edge of a blunt, open end applicator may be uncomfortable to a user, a pledget having a rounded insertion end is positioned in front of the blunt open end to provide better comfort.

For open insertion end applicators, when forming a rounded shape at the insertion end of a pledget, a strong axial force must be applied to the fibers of the pledget to achieve a true rounded, hemispherical shape. Since this axial force tends to exceed the columnar strength of the pledget, the pledget requires both axial and radial support about its outer surface during formation of the rounded insertion end. Existing methods utilize special apparatuses for providing the necessary axial and radial support to the pledget during formation of its rounded insertion end. Since the insertion end is formed before placement of the pledget within the applicator, the pledget must then be carefully inserted and secured in the applicator without damaging the formed insertion end. Such insertion can be very difficult.

II. Description of the Prior Art

Processes for providing support to the outer surface of a tampon pledget as its rounded insertion end is formed are known. For such processes, the rounded insertion end is formed before the pledget is positioned within a tampon applicator. For example, U.S. Pat. No. 2,077,231 to C. A. Fourness, et al., which issued on Apr. 13, 1937; U.S. Pat. No. 2,799,055 to J. A. Carrier, which issued on Jul. 16, 1957; U.S. Pat. No. 3,683,915 to J. A. Voss, which issued on Aug. 15, 1972; and, U.S. Pat. No. 4,685,178 to T. Nakanishi, which issued on Aug. 11, 1987.

Also, placement of a pledget in an applicator so that its insertion end projects beyond the insertion end of the applicator is also known. For example, U.S. Pat. No. 2,355,628 to V. Calhoun, which issued on Aug. 15, 1944; U.S. Pat. No. 2,386,590 to V. Calhoun, which issued on Oct. 9, 1945; U.S. Pat. No. 3,999,549 to R. P. Poncy, et al., which issued on Dec. 28, 1976; and, U.S. Pat. No. 4,077,408 to J. L. Murray, et al., which issued on Mar. 7, 1978. Each provides a pledget having a curved or semi-curved insertion end that is exposed at one end of the applicator.

Further, a special rim that supports a dispensed product, such as a suppository, in an applicator is described in U.S. Pat. No. 3,677,465 to J. A. Voss titled Applicator Tubes For Suppositories and the Like, which issued on Jun. 6, 1972. The patent provides a suppository dispenser having segments at the forward end of a cylindrical applicator that drop into a reduced neck portion of the suppository at right angles. Since the suppository is a substantially rigid item, the segments simply prevent the suppository from slipping out of the applicator and are designed to flare outward when the suppository is ejected from the applicator.

Although U.S. Pat. No. 3,667,465, cited above, suggests that its applicator may be used for tampon pledgets, it requires the formation of a substantially rigid neck portion and a tapered rear face that add to the complexity and cost of manufacturing such a pledget. Also, the patent provides that the back end of the suppository is tapered to facilitate insertion into the applicator from the insertion end, thus avoiding any damage to the insertion end of the suppository. However, the patent presumes that the insertion end is formed before placement within the applicator and does not provide a way to insert the suppository or pledget through the back end, opposite the blunt open end, of an applicator. In addition, this patent does not describe or suggest a method for forming a rounded insertion end of a suppository or pledget.

Short segments formed at the forward end of an applicator are known for tampon pledgets as well as suppositories. For example, U.S. Pat. No. 3,717,149 to B. P. Morane titled Injector Package For Catamenial Tampon, which issued on Feb. 20, 1973, provides short segments or petals at the blunt, open insertion end applicator which petals cover the insertion end of the pledget. Thus, similar to a petal tip applicator, the segments or petals are essentially confined to the forward edge of the pledget and do not provide any support to the pledget in the applicator.

Accordingly, none of the above patents describe or suggest a device or method for forming a rounded insertion end to a tampon pledget after the pledget has been assembled in the open insertion end of the tampon applicator.

SUMMARY OF THE INVENTION

Against the foregoing background, it is a primary object of the present invention to provide a open insertion end tampon applicator that facilitates the formation of a contoured shape, particularly a rounded or hemispherical shape, on the exposed fibers of a tampon pledget after assembly of the pledget in the applicator.

It is another object of the present invention to provide such a tampon applicator in which a supporting rim structure of the applicator firmly grips the pledget assembled therein during formation of the pledget's rounded insertion end and yet readily permits the pledget to eject from the applicator for use.

It is a further object of the present invention to provide such a tampon applicator in which conventional, high speed manufacturing techniques may continue to be used to produce the pledget before assembling the pledget in the applicator and forming its insertion end.

It is still another object of the present invention to provide such a tampon applicator in which assembly of the pledget in the applicator after formation of its insertion end, which assembly can be expensive and complex, is rendered unnecessary.

It is yet another object of the present invention to provide such a tampon applicator in which the rim structure of the applicator is tucked beneath the insertion end of the pledget.

To accomplish the foregoing objects and advantages, the present invention, in brief summary, is a configuration comprising a tampon pledget and a tampon applicator. The tampon pledget has an insertion end, a rear portion and an intermediate section located at an outer peripheral position of the tampon pledget between the insertion end and the rear portion. The tampon applicator has a rim structure at an end for supporting the tampon pledget at its intermediate section so that the rear portion of the tampon pledget is positioned in the tampon applicator and the insertion end of the tampon pledget is positioned outside of the tampon applicator. The rim structure has a frustum-shape that is tapered angularly inward toward the intermediate section of the tampon pledget at a predetermined angle away from the remainder of the tampon applicator for permitting the rear portion of the tampon pledget to eject from the tampon applicator and yet substantially hinder the insertion end of the tampon pledget from entering the tampon applicator when an axial force is applied to the insertion end of the tampon pledget.

The rounded insertion end of the tampon pledget is formed by the method comprising the initial step of forming a rim structure at one end of the tampon applicator that is tapered angularly inward from the remainder of the tampon applicator. The rim structure permits a tampon pledget to pass through the rim structure in a first axial direction and yet hinders the tampon pledget from passing through the rim structure in a second axial direction opposite the first axial direction. Then, the tampon pledget is supported within the rim structure such that an insertion end of the tampon pledget is exposed outside of the tampon applicator. Next, an axial force is applied to the insertion end of the tampon pledget to mold a portion of the insertion end over the rim structure and shape the remaining portion of the insertion end into a rounded form.

BRIEF DESCRIPTION OF THE DRAWINGS

The foregoing and still further the objects and advantages of the present invention will be more apparent from the following detailed explanation of the preferred embodiments of the invention in connection with the accompanying drawings:

FIG. 3 is another planar view of the first preferred rim structure of the applicator of FIG. 1, showing angular segments at a fully formed rim;

FIG. 3A is another planar view of the second preferred rim structure of the applicator of FIG. 1, showing rounded segments at the fully formed rim;

FIG. 5A and 5B are enlarged sectional views of the insertion end of the tampon applicator of FIGS. 4A and 4B; and FIG. 6 is a sectional view of the final configuration of the preferred embodiment produced by the steps of FIGS. 4A through 4E.

DETAILED DESCRIPTION OF THE PREFERRED EMBODIMENT

Figure 1:
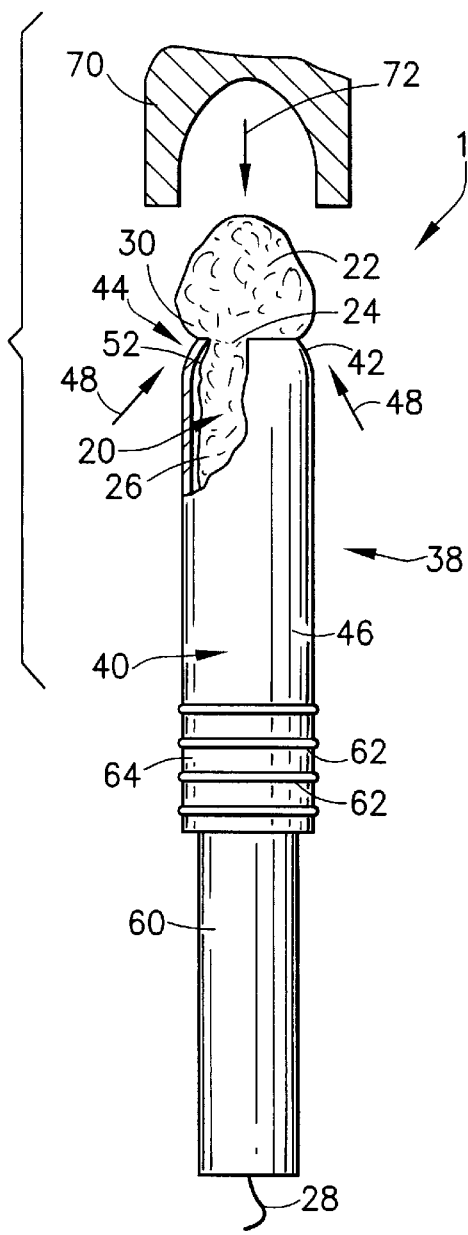
FIG. 1 is a planar view of the preferred embodiment of the tampon applicator of the present invention.

Referring to the figures and, in particular to FIG. 1, there is provided a tampon assembly which is generally represented by reference numeral 10. The tampon assembly 10 includes a tampon pledget 20 that is assembled in a tampon applicator 38. The tampon applicator 38 includes an applicator barrel 40 and an applicator plunger 60. A rim structure 44 is formed at the forward or open end 42 of the barrel 40 of the applicator 38. The tampon assembly 10 is shown with an upper left side of the applicator barrel 40 removed to show a portion of the tampon pledget 20 therein. The pledget 20 includes a body comprising an insertion end 22 that has a rounded, hemispherical shape to facilitate insertion into a vagina, an intermediate section 24 and a rear portion 26.

The formation of the rounded insertion end 22 requires a high amount of axial force 72 that is applied and subjected by a forming tool 70 to achieve the desired rounded, hemispherical shape. Heat and moisture may also be applied as part of this forming process. As shown in FIG. 1, the forming tool 70 is positioned adjacent to the insertion end of the tampon pledget 20. Although the tampon assembly 10 is shown vertically in FIG. 1, the position of the tampon assembly is not critical so long as the insertion end 22 of the pledget 20 is positioned accessible to the forming tool 70, and may be positioned horizontally as shown in FIGS. 4A through 4E.

The tampon assembly 10 shown in FIG. 1 is a completed product. The rounded insertion end 22 of the tampon pledget 20 has already been formed by the forming tool 70. Also, the insertion end 22 of the pledget 20 has an enlarged base 30 to cover the blunt, exposed edge at the open end 42 of the barrel 40.

Figure 2:
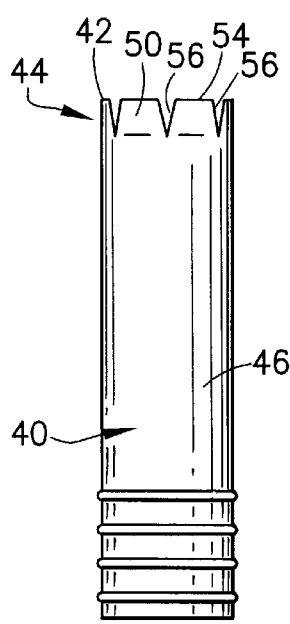
FIG. 2 is a planar view of a first preferred rim structure of the applicator of FIG. 1, showing angular segments at a partially formed rim.
Figure 2A:
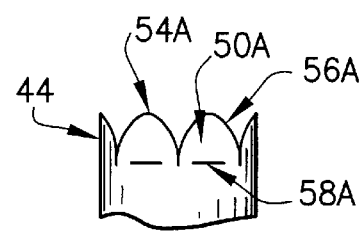
FIG. 2A is a planar view of a second preferred rim structure of the applicator of FIG. 1, showing rounded segments at the partially formed rim.

The barrel 40 is a predominantly cylindrical tube having ridges or finger grips 62 at the back end 64 and a rim structure 44 at the forward or open end 42. The rim structure 44 has a substantially frustum shape that tapers angularly and radially inward from the cylindrical body 46 of the barrel 40. The rim structure 44 may have an outer surface that is continuous (as shown in FIGS. 2 and 3) or segmented (as shown in FIGS. 2A and 3A). The pledget 20 is supported at the boundary or intermediate section within the rim structure 44 such that the insertion end 22 is exposed outside of the barrel 40 and the remaining portion of the rear portion 26 of the pledget is enclosed within the barrel.

The rim structure 44 produces a conical and angular counterforce or support represented by reference arrows 48 that supports the pledget 20 in the rim structure. This conical and angular support 48 counters the axial force 72 applied by the forming tool 70 to the insertion end 22 of the pledget 20. The rim structure 44 tapers angularly upward and inward at the intermediate section 24 of the pledget 20, thereby providing axial and radial support to the insertion end 22. Also, the rim structure 44 is capable of maintaining the intermediate section 24 therein against an axial force 72 strong enough to shape the insertion end 22 of the pledget 20. The axial force 72 varies with the application of heat and/or moisture during the forming process.

The rim structure 44 has a predetermined angle, from the cylindrical body 46 to the open end 42 about the intermediate section 24 of the pledget 20, that is large enough to substantially support the pledget in the rim structure and yet small enough to easily release the pledget for dispensing. For the preferred embodiment, for example, the predetermined angle is about 30 degrees to about 45 degrees, and preferably about 45 degrees. For the predetermined angle of the preferred embodiment, it has been determined that lesser angles are much less effective at supporting the pledget in the rim structure 44 whereas greater angles would require substantially more force to dispense the pledget from the rim structure.

The axial force 72 must not exceed the columnar strength of the barrel 40 to avoid damage to the barrel. Preferably, the axial force 72 is no greater than about 85% of the columnar strength of the barrel 40 in order to apply sufficient forming force to the insertion end 22 of the pledget 20 without the risk of damaging the barrel. One method of determining this preferred level of axial force 72 is to apply increasingly the force to the insertion end 22 of the pledget 20 until the barrel 40 begins to distort and, then, reducing the axial force by about 15% to reach the preferred level of axial force.

When the forming tool 70 applies the axial force 72 to the insertion end 22, an inner portion of the insertion end may attempt to pass through the open aperture surrounding the intermediate section 24. However, the conical and angular support 48 produced by the rim structure 44 retains the intermediate section 24 within the rim structure and prevents the insertion end 22 from entering the inside of the barrel 40. The rim structure 44 also permits the pledget 20 to eject outward from the barrel 40 due to its tapered inner surface 52 of the rim structure 44.

It is to be understood that the present invention may utilize a wide variety of different forming tools to form the rounded insertion end of the pledget. For example, an alternative forming tool is set forth in co-pending U.S. patent application titled METHOD FOR POST FORMING A ROUNDED INSERTION END OF A TAMPON PLEDGET OF AN OPEN-ENDED APPLICATOR, filed on even date, which application is owned by the assignee of the present invention. This co-pending application is incorporated herein by reference.

The tampon plunger 60 is slidably positioned within barrel 40 so that a portion of the plunger extends from the back end 64 of the barrel. A draw string 28 extends from the rear portion 26 of the pledget 20 (not shown), passes through the hollow inner core of the plunger 60, and is exposed beyond the back end 64 of the plunger.

The rim structure 44 of the present invention may be formed having a wide variety of structural supports and elements so long as the rim structure supports the pledget 20 against the axial force 72 applied by the forming tool 70 when forming the insertion end 22 of the pledget. As examples, a first preferred rim structure is shown in FIGS. 2 & 3, and a second preferred rim structure is shown in FIGS. 2A & 3A.

Referring to FIGS. 2 and 2A, a plurality of small separate, hinged segments 50 & 50A which form the rim structure 44 & 44A are provided around the open end 42 & 42A of the barrel 40. In FIG. 2, each segment 50 of the first preferred form has a trapezoidal shape bordered by a distal edge 54, two lateral tapered sides 56 and a hinge 58. The distal edge 54 of each segment 50 is parallel to the hinge 58. In FIG. 2A, each segment 50A of the second preferred form has a radius tip 54A, two lateral tapered sides 56A and a hinge 58A. The hinge 58A is directly opposed to the radius tip 54A located at the root of the petal segment 50A.

As shown in FIGS. 2 and 2A, the lateral tapered sides 56 & 56A of each segment 50 & 50A are angled inward toward the distal edge 54 or distal radius 54A. Preferably, the lateral tapered sides 56 & 56A are formed by removing intervals of wedges (not shown) from the open end 42 of the barrel 40, and the hinge 58 is formed by perforating the lower portion of each segment 50 & 50A. Before formation of the rim structure 44 is completed, as shown in FIG. 2, the segments 50 & 50A are flush or even with the outer surface of the barrel 40.

Referring to FIG. 3 and 3A, the rim structure 44 is completely formed by bending each segment 50 & 50A inward at the hinges 58 & 58A so that the lateral sides 56 & 56A of the segments come in full or partial contact with each other. The distal edges 54 or distal radius 54A of the segments 50 & 50A come together to form a continuous circular edge (shown in FIG. 3) or scalloped edge (shown in FIG. 3A) at the top portion of the rim structure 44 & 44A. The lateral sides 56 & 56A abut against each other to provide radial support for the rim structure 44 & 44A. They also provide axial support that counters the axial force 72 applied to the rim structure 44 & 44A. In this manner, the segments 50 & 50A provide the requisite radial and axial support at the intermediate section 24 of the pledget 20 during the formation of the insertion end 22. The segments 50 & 50A grip the intermediate section 24 firmly enough, and at a proper angle, to permit the formation of the rounded insertion end 22 after the pledget 20 has been inserted into the barrel 40.

The pledget 20 is made of a material having a high liquid absorbent quality. Such materials include rayon, cotton, cotton/rayon blends and paper filler type materials. For the preferred embodiment, the pledget 20 includes a plurality of fibers 30 extending the length of the pledget in order to provide a wicking channel to draw fluids, particularly menstrual fluids, away from the insertion end 22 and towards the rear portion 26. The pledget 20 is, preferably, made of a cotton/rayon blend.

Although the material compositions of the barrel 42 and plunger 44 of the applicator 40 may vary, it is preferred that they be made of similar materials. The most common materials are the light yet semi-rigid type of materials, including plain or coated paper or cardboard or plastic. The coatings that may be used on the paper or cardboard include wax, plastic and cellulose.

The forming tool 70 may be made of a wide variety of materials that are hard enough to form a rounded, hemispherical shape at the insertion end 22 of the pledget 20. In addition, the forming tool 70 may be coated with steel, brass, copper or plastic in order to prevent rust and oxidation. Furthermore, the forming tool 70, and in particular the aluminum forming tool, may be anodized to prevent oxidation. The preferred composition of the forming tool is aluminum or stainless steel.

Optionally, the forming tool may be heated within a temperature range of about 150 degrees to about 310 degrees Fahrenheit for about 3 to about 15 seconds. The temperature and time of heating will depend upon the properties of the fiber materials being formed by the forming tool. Preferably, the forming tool will be heated a temperature of about 300 degrees Fahrenheit for about 7 seconds.

Referring to FIGS. 4A through 4E, there is shown the five major steps for forming the rounded insertion end 22 of the tampon pledget 20 of the preferred embodiment. Before the insertion end 22 is formed, the trapezoid-shaped segments 44 is first constructed at the rim structure 44, as shown in FIG. 2. Also, the rim structure 44 must tapered angularly inward from the outer surface of the barrel 40 so that the segments 44 are adjacent and continuous with one another, as shown in FIG. 3.

Figure 4A:
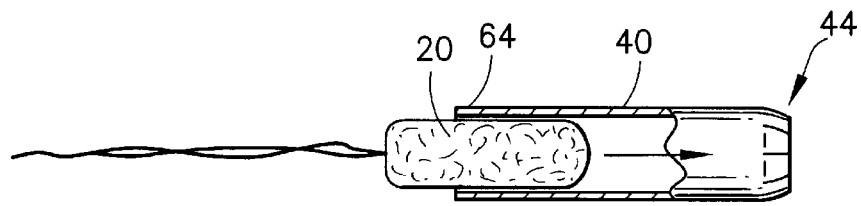
FIG. 4A through 4E are exploded, sectional views of the step-by-step method of the preferred embodiment of FIG. 1.
Figure 4B:
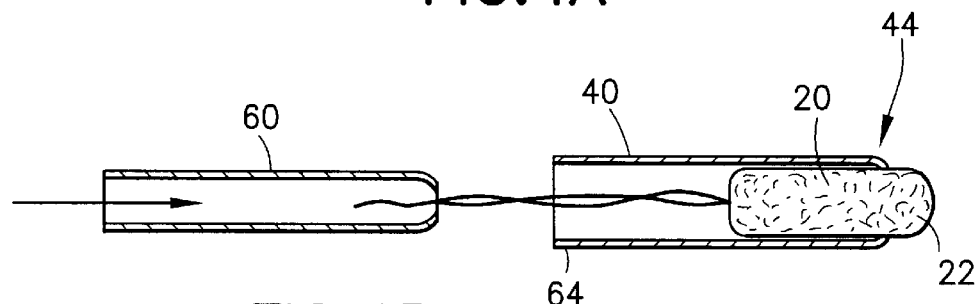
Figure 4C:
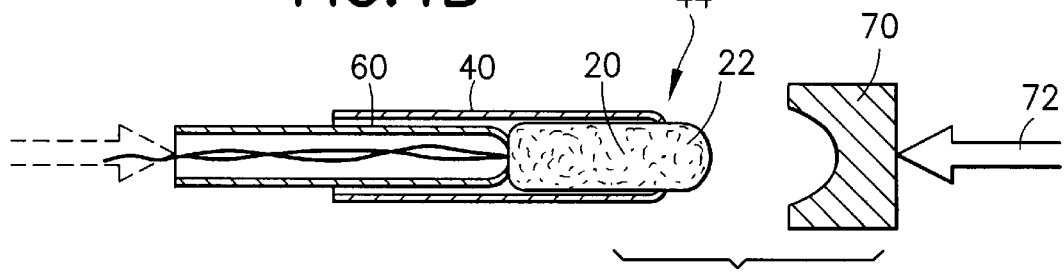
Figure 4D:
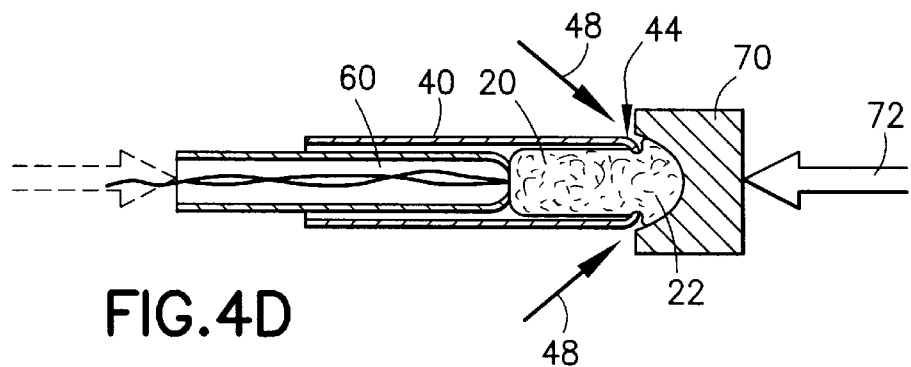

As shown in FIG. 4A, the pledget 20 is inserted into the barrel 40 through the back end 64 opposite the rim structure 44. The pledget 20 is supported at its intermediate section 24 within the rim structure 44 such that the insertion end 22, not yet formed, is exposed outside of the barrel 40, as shown in FIG. 4B. Thus, the rear portion 26 of the pledget 20 is positioned in the applicator 38 and the insertion end 22 is positioned outside of the applicator. The plunger 60 is then inserted through the back end 64 into the barrel 40 and is positioned adjacent to the rear portion 26 of the pledget 20, as shown in FIG. 4B. The plunger 60 axially supports the pledget 20 against any axial force received in subsequent steps, such as the axial force 72 subjected by the forming tool 70, as shown in FIGS. 4C and 4D. This axial support from the plunger 60 is not necessary for the present invention, but simply supplements the conical and angular support 48 of the rim structure 44.

As shown in FIGS. 4C and 4D, the forming tool 70 is then applied to the non-formed insertion end 22 of the pledget 20 that is assembled in the applicator 38. The axial force 72 applied by the forming tool 70 causes a portion of the insertion end 22 to expand over the rim structure 44 and, thus, forms the enlarged base 30 (shown in FIG. 1) of the insertion end 22. At s the same time, the remaining frontal portion of the insertion end 22 is shaped into a rounded, hemispherical form. The conical and angular counterforces or support 48 provided by the rim structure 44 counters the axial force 72 of the forming tool 70 and retains the pledget 20 in the desired position within the rim structure during formation of the rounded insertion end 22.

Figure 4E:
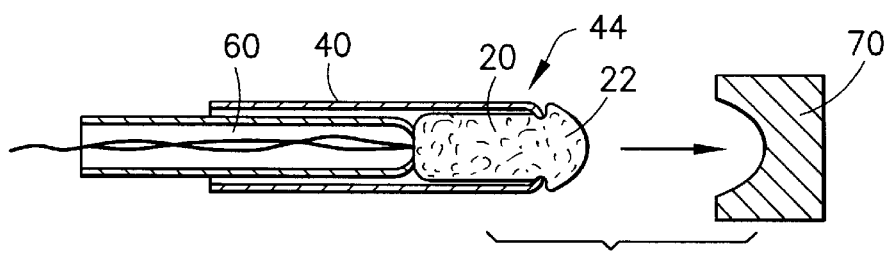

Referring to FIG. 4E, the forming tool 70 is drawn away from the insertion end 22 of the pledget 20 after formation of the rounded insertion end. At this point, the tampon assembly 10 is essentially complete and ready for packing and distribution without the need for any further assembly or manufacturing.

Referring to FIGS. 5A and 5B, there are shown enlarged views of the insertion end 22 corresponding the FIGS. 4A and 4B, respectively. In particular, FIG. 5A shows the rim structure 44 before the pledget 20 has been inserted, and FIG. 5B shows the rim structure after the pledget has been supported therein. As shown in FIG. 5A, the lateral sides 56 of each segment 50 are in contact with each other and form the continuous rim structure 44. However, as shown in FIG. 5B, the segments 50 flex outward in order to adapt to the outer peripheral surface of the pledget 20. In this manner, the rim structure 44 has a strong yet flexible grip at the intermediate section 24 of the pledget 20 which is necessary for the formation of the insertion end 22.

Referring to FIG. 6, the final assembly of the tampon pledget 20 and the tampon applicator 38 combination of the preferred embodiment is shown. For insertion of the pledget 20 into a vagina, the plunger 60 is pressed through the back end 64 of the barrel 40 to apply an axial pressure or force to the rear portion 26 of the pledget 20. Due to the tapered and angular form of the inner surface 52 of the rim structure 44, the rear portion 26 of the pledget 20 easily traverses the rim structure and ejects from the barrel 40 of the applicator 38.

The invention having been thus described with particular reference to the preferred forms thereof, it will be obvious that various changes and modifications may be made therein without departing from the spirit and scope of the invention as defined in the appended claims.

Wherefore, we claim:

1. A tampon assembly comprising:
    a tampon pledget having an insertion end, a rear portion and an intermediate section extending for a length between said insertion end and said rear portion,
    a tampon applicator barrel having a rim structure located peripherally about a first end thereof for supporting said tampon pledget at said intermediate section, wherein said rear portion of said tampon pledget is positioned in said tampon applicator barrel and said insertion end of said tampon pledget is positioned outside of said tampon applicator barrel,
    said rim structure having a frustum-shape that is tapered angularly inward toward said intermediate section of said tampon pledget at a predetermined angle away from a rear portion of said tampon applicator barrel, wherein said frustum-shape tapers angularly inward to a reduced width opening and said opening is smaller than a largest diameter of said insertion end, and
    wherein said rim structure permits said insertion end of said tampon pledget to pass through said first end of said tampon applicator barrel and ejection of said tampon pledget from said tampon applicator barrel and yet prevents said insertion end of said tampon pledget from entering into said tampon applicator barrel when an axial force is applied to said insertion end during formation of said insertion end.

2. The tampon assembly of claim 1, wherein said rim structure comprises a plurality of segments located peripherally about said first end of said tampon applicator barrel, each of said plurality of segments being directed angularly inward toward said intermediate section of said tampon pledget.

3. The tampon assembly of claim 2, wherein each of said plurality of segments has a distal edge for contacting said intermediate section of said tampon pledget and a substantially opposite and parallel hinge having a length that is longer than a length of said distal edge.

4. The tampon assembly of claim 2, wherein each of said plurality of segments has a distal radius for contacting said intermediate section of said tampon pledget and said plurality of segments come together to form a scalloped edge at said opening.

5. The tampon assembly of claim 1, wherein said predetermined angle of said frustum-shape, from said rear portion of said tampon applicator barrel to said intermediate section of said tampon pledget, is about 30 degrees to about 45 degrees.

6. The tampon assembly of claim 5, wherein said predetermined angle is about 45 degrees.

7. The tampon assembly of claim 1, wherein said rim structure is capable of maintaining said intermediate section of said tampon pledget in said tampon applicator barrel against the axial force when the axial force is about 15% less than the columnar strength of said tampon applicator barrel.

8. The tampon assembly of claim 1, wherein said insertion end of said tampon pledget is radially expanded relative to said rear portion of said tampon pledget.

9. A tampon assembly including a tampon pledget having an insertion end, a rear portion and an intermediate section located at an outer peripheral position of the tampon pledget between the insertion end and the rear portion, said tampon assembly comprising:
    a tampon applicator barrel having a rim structure at a first end for supporting the tampon pledget at the intermediate section, and having a remainder portion connected to the intermediate section, wherein the rear portion of the tampon pledget is positioned in said tampon applicator barrel and the insertion end of the tampon pledget is positioned outside of said tampon applicator barrel;
    said rim structure having a frustum-shape that is tapered angularly inward toward the intermediate section at a predetermined angle away from the remainder portion of said tampon applicator barrel, whereby said rim structure permits the rear portion of the tampon pledget to eject from said tampon applicator barrel and yet substantially hinders the insertion end of the tampon pledget from entering said tampon applicator barrel when an axial force is applied to the insertion end during formation of the insertion end;

said rim structure comprises a plurality of segments located peripherally about said first end of said tampon applicator barrel, each of said plurality of segments being directed angularly inward toward the intermediate section of the tampon pledget, each of said plurality of segments having at least two tapered, lateral sides that abut the lateral sides of each pair of adjacent segments to form said frustum-shaped rim structure.

* * * * *